United States Patent [19]

Murakami et al.

[11] Patent Number: 5,734,043
[45] Date of Patent: Mar. 31, 1998

[54] SEPARATING AGENT FOR OPTICAL ISOMERS

[75] Inventors: Tatsushi Murakami; Nanami Nishida, both of Hyogo, Japan

[73] Assignee: Daicel Chemical Industries, Ltd., Osaka, Japan

[21] Appl. No.: 582,987

[22] PCT Filed: Apr. 27, 1995

[86] PCT No.: PCT/JP95/00844

§ 371 Date: Dec. 29, 1995

§ 102(e) Date: Dec. 29, 1995

[87] PCT Pub. No.: WO95/31420

PCT Pub. Date: Nov. 23, 1995

[30] Foreign Application Priority Data

May 17, 1994 [JP] Japan .................. 6-102548

[51] Int. Cl.$^6$ .................. C08B 3/00; C08B 30/00
[52] U.S. Cl. .................. 536/30; 536/4.1; 536/18.5; 536/45; 536/55.1; 536/56; 536/58; 536/102; 536/123.1; 523/218; 523/219; 521/54; 521/55; 521/57; 521/84.1; 521/109.1
[58] Field of Search .................. 536/18.5, 30, 55.1, 536/56, 58, 45, 102, 123.1, 124, 125, 4.1; 523/218, 219; 521/54, 55, 57, 84.1, 109.1

[56] References Cited

U.S. PATENT DOCUMENTS

| 4,683,341 | 7/1987 | Ishii et al. . | |
| 5,302,633 | 4/1994 | Kimata et al. | 523/218 |
| 5,587,467 | 12/1996 | Morakami et al. | 536/18.5 |

FOREIGN PATENT DOCUMENTS

| 0 147 804 | 7/1985 | European Pat. Off. . |
| 6-206895 | 7/1994 | Japan . |
| 6-329561 | 11/1994 | Japan . |

OTHER PUBLICATIONS

J. Am. Chem. Soc., 1984, vol. 106, No. 18, pp. 5357–5359.

Primary Examiner—James O. Wilson
Attorney, Agent, or Firm—Flynn, Thiel, Boutell & Tanis, P.C.

[57] ABSTRACT

A separating agent which, when used as the packing material for reverse-phase liquid chromatography, has excellent baseline stability in the mobile phase and an increased number of steps of the detected peak in the measurement is provided. The agent comprises a polysaccharide derivative supported on a silica gel having surface silanol groups treated with a silylating agent having an aralkyl group.

12 Claims, No Drawings

SEPARATING AGENT FOR OPTICAL ISOMERS

FIELD OF INDUSTRIAL APPLICATION

The present invention relates to a separating agent for optical isomers, particularly to a separating agent useful for the optical resolution of racemic compounds, which comprises a polysaccharide derivative supported on a silica gel having its surface silanol treated with a silylating agent having an aralkyl group.

PRIOR ART

It is known that a packing material comprising a polysaccharide derivative supported on a silica gel is useful as a separating agent for optical isomers from racemic compounds (Y. OKAMOTO, M. KAWASHIMA and K. HATADA, J. Am. Chem. Soc., 106, 5357, 1984). Such a separating agent is supported on a carrier, such as a silica gel, wherein the surface silanols causative of specific adsorption or other troubles have been suitably treated, e.g., an aminopropylated silica gel or a carbamoylated silica gel obtained by further reacting the aminopropyl groups with 3,5-dimethylphenyl isocyanate. However, when such a separating agent is used as a packing material for reversed-phase liquid chromatography, it has defects such as the instability of the base line in a liquid chromatograph, a reduced number of theoretical plates for a detected peak in the measurement, and the elution of a low-molecular portion of the polysaccharide derivative depending on the composition of the mobile phase. One of the reasons for such defects is supposedly a poor affinity of the silylating agent on the silica gel surface for the polysaccharide derivative, in other words, the instability of the polysaccharide derivative on the carrier.

Under these circumstances, there has been demanded a separating agent which, when used as a packing material for reversed-phase liquid chromatography, has excellent base-line stability of the and number of theoretical plates in the column, in other words, there is an excellent affinity of the polysaccharide derivative for the silylating agent and, also stability of the polysaccharide on the carrier.

DISCLOSURE OF THE INVENTION

After intensive investigations made for the purpose of developing a separating agent free from the above-described defects and capable of exhibiting the advantageous properties of the polysaccharide derivative to the full, the inventors have attained the present invention.

Namely, the present invention provides a separating agent for optical isomers, which comprises a polysaccharide derivative supported on a silica gel having surface silanol groups treated with a silylating agent having an aralkyl group.

Preferably, the surface silanol groups of the silica gel are treated by reacting the silica gel with a silylating agent in the present invention.

The present invention further provides a process for separating optical isomers from racemic compounds with the above-described separating agent for optical isomers, preferably by reversed-phase liquid chromatography, wherein an aqueous liquid such as water or an alcohol is used.

The polysaccharide used in the present invention may be any of synthetic, natural and modified natural polysaccharides as long as it is optically active. The polysaccharide is preferably one having a high regularity in its bonding manner. Examples of the polysaccharides include $\beta$-1,4-glucan (cellulose), $\alpha$-1,4-glucan (amylose or amylopectin), $\alpha$-1,6-glucan (dextran), $\beta$-1,6-glucan (pustulan), $\beta$,1,3-glucan (such as curdlan or shizophyllan), $\alpha$-1,3-glucan, $\beta$-1,2-glucan (Crown Gall polysaccharide), $\beta$-1,4-galactan, $\beta$-1,4-mannan, $\alpha$-1,6-mannan, $\beta$-1,2-fructan(inulin), $\beta$-2,6-fructan (levan), $\beta$-1,4-xylan, $\beta$-1,3-xylan, $\beta$-1,4-chitosan, $\beta$-1,4-N-acetylchitosan (chitin), pullulan, agarose and alginic acid. They also include amylose-containing starches. Among them, preferred are polysaccharides which can be easily obtained in a highly pure state, such as cellulose, amylose, $\beta$-1,4-chitosan, chitin, $\beta$-1,4-mannan, $\beta$-1,4-xylan, inulin and curdlan, and particularly preferred are cellulose and amylose.

The number-average degree of polymerization (average number of pyranose or furanose rings contained in a molecule) of the polysaccharides is at least 5, preferably at least 10. Although the upper limit thereof is not particularly provided, it is preferably 500 from the viewpoint of ease of handling.

The polysaecharide derivatives used in the present invention include ester derivatives and carbamate derivatives thereof obtained by reacting the hydroxyl or amino groups of the polysaccharide with a compound having a functional group reactive with the hydroxyl or amino group by a well-known method to form ester or urethane bonds.

The compound having a functional group which reacts with the hydroxyl or amino group may be any compound selected from among isocyanic acid derivatives, carboxylic acids, esters, acid halides, acid amides, halides, epoxides, aldehydes, alcohols and compounds having a leaving group. They are, for example, aliphatic, alicyclic, aromatic and heteroaromatic compounds. Particularly preferred are benzoyl chlorides and derivatives thereof represented by the following formula (2) and phenyl isocyanates and derivatives thereof represented by the following formula (3):

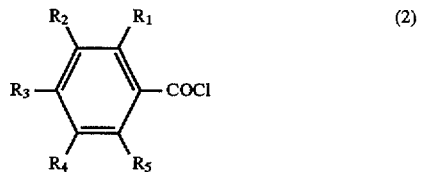

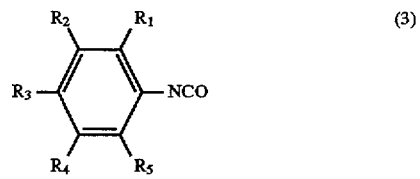

(wherein $R_1$, $R_2$, $R_3$, $R_4$ and $R_5$ each represent a hydrogen atom, an alkyl group having 1 to 8 carbon atoms or a halogen atom).

The particle diameter of the silica gel carrier used in the present invention is 1 μm to 10 mm, preferably 1 μm to 1,000 μm, and still preferably 1 μm to 300 μm. The average pore diameter is 10 A to 100 μm, preferably 50 Å to 50,000 Å.

The silylating agents having an aralkyl group and used for the treatment of the surface silanol groups of the silica gel in the present invention are compounds of the following general formula (1):

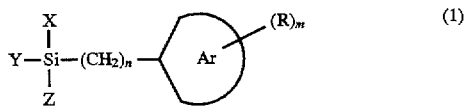

(wherein at least one of X, Y and Z is Cl or an alkoxy group having 1 or 2 carbon atoms and the rest are methyl or ethyl group(s), n represents an integer of 1 to 8, R represents an alkyl or alkoxy group having 1 to 4 carbon atoms, m represents 0 or 1, and

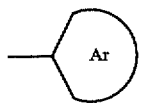

represents an aromatic group having 6 to 14 carbon atoms).

In the silylating agent represented by the general formula (1) used in the present invention, at least one of X, Y and Z is a chlorine atom or an alkoxy group having 1 or 2 carbon atoms such as a methoxy or ethoxy group, and the rest(s) is(are) a methyl or ethyl group. Namely, the silylating agent must have at least one functional group capable of reacting with the surface silanol groups of the silica gel to form a bond. In the general formula (1), n represents an integer of 1 to 8, preferably 2 to 4, R represents an alkyl or alkoxy group having 1 to 4 carbon atoms such as a methyl, propyl, isopropyl, methoxy, propoxy or isopropoxy group which may be either linear or branched, and m represents 0 or 1. In the general formula (1),

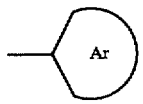

represents an aromatic group having 6 to 14 carbon atoms, such as a phenyl, naphthyl or anthryl group, preferably a phenyl group.

After treatment of the surface silanol groups of the silica gel with the silylating agent having an aralkyl group in the present invention, the gel may be further end-capped with a commercially available end-capping agent capable of introducing a trimethylsilyl group, such as N,O-bis (trimethylsilyl)acetamide, trimethylchlorosilane or hexamethyldisilazane.

The surface treatment of the silica gel with the silylating agent having an aralkyl group can be conducted by an ordinary surface treatment method with silica gel. For example, the silica gel is reacted with the silylating agent having an aralkyl group under reflux of a solvent such as toluene.

The polysaccharide derivative is supported on the silica gel surface-treated with the silylating agent having an aralkyl group as described above by a physical method in the present invention. As a specific method, the polysaccharide derivative is dissolved in a solvent therefor and thoroughly mixed with the silica gel surface-treated with the silylating agent having an aralkyl group, and the solvent is distilled off under reduced pressure, under heating or in a gas stream.

Although the separating agent of the present invention is usable in ordinary chromatography such as gas chromatography, liquid chromatography or thin-layer chromatography to separate various optical isomers, it is desirably applied in liquid chromatography. Although it is usable in both normal and reversed phases in liquid chromatography, it is used particularly preferably in reversed phase.

The separating agent obtained by supporting the polysaccharide derivative on the silica gel having the surface silanol groups treated with the silylating agent having an aralkyl group in the present invention has excellent baseline stability in the mobile phase and is increased in the number of the theoretical plates for a detected peak in the measurement when it is used as the packing material for reversed-phase liquid chromatography. Thus, the separating agent of the present invention is an epoch-making one capable of widening the use of the separating agent comprising the supported polysaccharide derivative.

EXAMPLES

The following Examples will further illustrate the present invention, which by no means limit the invention.

Example 1

(1) Reaction for treatment of the surface silanol groups of silica gel:

20 g of porous silica gel (SP-1000; a product of Daiso Co., Ltd.) was thoroughly dehydrated and dried, and then reacted with 10 ml of 3-phenylpropyldimethylchlorosilane (a product of PETRARCH SYSTEMS) under reflux of toluene in a nitrogen atmosphere for 20 h. The reaction product was separated by filtration through a glass filter, washed with toluene and methylene chloride, and dried.

(2) Preparation of separating agent comprising cellulose derivative supported on silica gel:

A dope comprising 2.4 g of cellulose tris(4-methylbenzoate) was uniformly sprinkled on 9.6 g of the surface-treated silica gel obtained in the above-described step (1). The solvent was distilled off to support cellulose tris(4-methylbenzoate) on the silica gel, which was then washed with methanol, diisopropyl ether and n-hexane, and dried.

(3) Preparation of column for optical resolution:

The separating agent comprising the cellulose derivative supported on the silica gel as prepared in the above-described step (2) was used as the packing material and packed in a stainless steel column having a length of 15 cm and an inner diameter of 0.46 cm by the slurry packing procedure.

(4) Evaluation of capacity of column for optical resolution:

The capacity of the column for optical resolution obtained in the above-described step (3) was evaluated by using JASCO 875-UV (manufactured by JASO Corp). The eluent used was a water/acetonitrile (60/40) mixture, and the conditions comprised a flow rate of 0.3 ml/min, a temperature of 25° C., a sample concentration of 1000 ppm, and an amount of the sample poured therein of 5 μl. The results of the optical resolution experiment on α-naphthylethanol used as the standard compound are given in Table 1.

The terms in the Table are defined as follows:

volume ratio (k')=[(retention time of antipode)−(dead time)]/(deadtime)

separation factor (α)=(volume ratio of more strongly adsorbed antipode)/(volume ratio of more weakly adsorbed antipode)

resolution (Rs)=[2×(distance between peak of more strongly adsorbed antipode and peak of more weakly adsorbed antipode)]/(total of band widths of both peaks)

number of theoretical plates (N/m)=number of theoretical plates determined by the tangential method from pre-peak of each racemic compound stability of baseline: the base line is judged to have been stabilized when the baseline is kept horizontal for 30 min stabilization time: time taken for the stabilization of the baseline when the liquid is passed through the mobile phase (for example, when the baseline lies horizontal 30 min after the beginning of the passage of the liquid through the mobile phase, the stabilization time is 1 h).

Example 2

(1) Reaction for treatment of the surface silanol groups of silica gel:

20 g of porous silica gel (SP-1000; a product of Daiso Co., Ltd.) was thoroughly dehydrated and dried, and then reacted with 10 ml of methyl(2-phenethyl)-dichlorosilane (a product of PETRARCH SYSTEMS) and 7.4 ml of pyridine under reflux of toluene in a nitrogen atmosphere for 14 h. The reaction product was separated by filtration through a glass filter, washed with toluene, methylene chloride, ethanol and hexane, and dried.

(2) Preparation of separating agent comprising cellulose derivative supported on silica gel:

A separating agent comprising cellulose tris(4-methylbenzoate) supported on silica gel was prepared in the same manner as that of Example 1 (2) except that the surface-treated silica gel obtained in the above-described step (1) was used.

(3) Preparation of column for optical resolution:

A column for optical resolution was prepared in the same manner as that of Example 1 (3) except that the separating agent obtained in the above-described step (2) was used.

(4) Evaluation of capacity of column for optical resolution:

The capacity of the column for optical resolution obtained in the above-described step (3) was evaluated in the same manner as that of Example 1 (4). The results of the optical resolution experiment on α-naphthylethanol used as the standard compound are given in Table 1.

Example 3

(1) Reaction for treatment of the surface silanol groups of silica gel:

20 g of porous silica gel (SP-1000; a product of Daiso Co., Ltd.) was thoroughly dehydrated and dried, and then reacted with 10 ml of 3-(4-methoxyphenyl)-propylmethyldichlorosilane (a product of PETRARCH SYSTEMS) and 6.1 ml of pyridine under a reflux of toluene in a nitrogen atmosphere for 14 h. The reaction product was separated by filtration through a glass filter, washed with toluene, methylene chloride, ethanol and hexane, and dried.

(2) Preparation of separating agent comprising cellulose derivative supported on silica gel:

A separating agent comprising cellulose tris-(4-methylbenzoate) supported on silica gel was prepared in the same manner as that of Example 1 (2) except that the surface-treated silica gel obtained in step (1) was used.

(3) Preparation of column for optical resolution:

A column for the optical resolution was prepared in the same manner as that of Example 1 (3) except that the separating agent obtained in the above-described step (2) was used.

(4) Evaluation of capacity of column for optical resolution:

The capacity of the column for optical resolution obtained in the above-described step (3) was evaluated in the same manner as that of Example 1 (4). The results of the optical resolution experiment on α-naphthylethanol used as the standard compound are given in Table 1.

Example 4

(1) Reaction for treatment of the surface silanol groups of slica gel:

8 g of silica gel surface-treated once and obtained in Example 2 (1) was thoroughly dehydrated and dried, and then reacted with 0.8 ml of N,O-bis-(trimethylsilyl) acetamide (a product of Nacalai Tesque, Inc.) under a reflux of toluene in a nitrogen atmosphere for 4 h. The reaction product was separated by filtration through a glass filter, washed with toluene and methanol, and dried.

(2) Preparation of separating agent comprising cellulose derivative supported on silica gel:

A separating agent comprising cellulose tris(4-methylbenzoate) supported on silica gel was prepared in the same manner as that of Example 1 (2) except that the surface-treated silica gel obtained in the above-described step (1) was used.

(3) Preparation of column for optical resolution:

A column for optical resolution was prepared in the same manner as that of Example 1 (3) except that the separating agent obtained in the above-described step (2) was used.

(4) Evaluation of capacity of column for optical resolution:

The capacity of the column for optical resolution obtained in the above-described step (3) was evaluated in the same manner as that of Example 1 (4). The results of the optical resolution experiment on α-naphthylethanol used as the standard compound are given in Table 1.

Comparative Example 1

(1) Reaction for treatment of the surface silanol groups of silica gel:

20 g of porous silica gel (SP-1000; a product of Daiso Co., Ltd.) was thoroughly dehydrated and dried, and then reacted with 10 ml of (N,N-dimethyl-3-aminopropyl) trimethoxysilane (a product of PETRARCH SYSTEMS) under a reflux of toluene in a nitrogen atmosphere for 9 h. The reaction product was separated by filtration through a glass filter, washed with toluene and methylene chloride, and dried.

(2) Preparation of separating agent comprising cellulose derivative supported on silica gel:

A dope comprising 2.4 g of cellulose tris(4-methylbenzoate) was uniformly sprinkled on 9.6 g of the surface-treated silica gel obtained in the above-described step (1). The solvent was distilled off to support cellulose tris(4-methylbenzoate) on the silica gel, which was then washed with methanol, diisopropyl ether and n-hexane, and dried.

(3) Preparation of column for optical resolution:

The separating agent comprising the cellulose derivative supported on the silica gel as prepared in the above-described step (2) was used as the packing material and packed in a stainless steel column having a length of 15 cm and an inner diameter of 0.46 cm by the slurry method.

(4) Evaluation of capacity of column for optical resolution:

The capacity of the column for optical resolution obtained in the above-described step (3) was evaluated in the same manner as that of Example 1 (4). The results of the optical resolution experiment on α-naphthylethanol used as the standard compound are given in Table 2.

Comparative Example 2

(1) Reaction for treatment of the surface silanol of silica gel:
 20 g of porous silica gel (SP-1000; a product of Daiso Co., Ltd.) was thoroughly dehydrated and dried, and then reacted with 10 ml of isobutyltrimethoxysilane (a product of PETRARCH SYSTEMS) under a reflux of toluene in a nitrogen atmosphere for 14 h. The reaction product was separated by filtration through a glass filter, washed with toluene and methylene chloride, and dried.

(2) Preparation of separating agent comprising cellulose derivative supported on silica gel:

A separating agent comprising cellulose tris(4-methylbenzoate) supported on silica gel was prepared in the same manner as that of Comparative Example 1 (2) except that the surface-treated silica gel obtained in the above-described step (1) was used.

(3) Preparation of column for optical resolution:

A column for optical resolution was prepared in the same manner as that of Comparative Example 1 (3) except that the separating agent obtained in the above-described step (2) was used.

(4) Evaluation of capacity of column for optical resolution:

The capacity of the column for optical resolution obtained in the above-described step (3) was evaluated in the same manner as that of Example 1 (4). The results of the optical resolution experiment on α-naphthylethanol used as the standard compound are given in Table 2.

Comparative Example 3

(1) Reaction for treatment of the surface silanol of silica gel:

A porous silica gel was treated with APS (aminopropylsilane) by an ordinary method.

(2) Preparation of separating agent comprising cellulose derivative supported on silica gel:

A separating agent comprising cellulose tris(4-methylbenzoate) supported on silica gel was prepared in the same manner as that of Comparative Example 1 (2) except that the surface-treated silica gel obtained in the above-described step (1) was used.

(3) Preparation of column for optical resolution:

A column for optical resolution was prepared in the same manner as that of Comparative Example 1 (3) except that the separating agent obtained in the above-described step (2) was used.

(4) Evaluation of capacity of column for optical resolution:

The capacity of the column for optical resolution obtained in the above-described step (3) was evaluated in the same manner as that of Example 1 (4). The results of the optical resolution experiment on α-naphthylethanol used as the standard compound are given in Table 2.

Comparative Example 4

(1) Reaction for treatment of the surface silanol of silica gel:

A porous silica gel was treated with ODS (octadecylsilane) by an ordinary method.

(2) Preparation of separating agent comprising cellulose derivative supported on silica gel:

A separating agent comprising cellulose tris(4-methylbenzoate) supported on silica gel was prepared in the same manner as that of Comparative Example 1 (2) except that the surface-treated silica gel obtained in the above-described step (1) was used.

(3) Preparation of column for optical resolution:

A column for optical resolution was prepared in the same manner as that of Comparative Example 1 (3) except that the separating agent obtained in the above-described step (2) was used.

(4) Evaluation of capacity of column for optical resolution:

The capacity of the column for optical resolution obtained in the above-described step (3) was evaluated in the same manner as that of Example 1 (4). The results of the optical resolution experiment on α-naphthylethanol used as the standard compound are given in Table 2.

TABLE 1

| Type of column | Ex. 1 | Ex. 2 | Ex. 3 | Ex. 4 |
|---|---|---|---|---|
| Stabilization time (hrs) | 1.0 | 1.0 | 1.0 | 1.0 |
| Separation factor (α) | 1.43 | 1.44 | 1.42 | 1.46 |
| Resolution (Rs) | 5.91 | 6.40 | 5.91 | 6.10 |
| Number of theoretical plates (N/m) | 52000 | 60000 | 55000 | 48000 |

TABLE 2

| Type of column | Comp. Ex. 1 | Comp. Ex. 2 | Comp. Ex. 3 | Comp. Ex. 4 |
|---|---|---|---|---|
| Stabilization time (hrs) | 2.0 | 1.0 | 5.0 | 1.0 |
| Separation factor (α) | 1.47 | 1.47 | 1.47 | 1.38 |
| Resolution (Rs) | 4.96 | 4.67 | 5.21 | 3.64 |
| Number of theoretical plates (N/m) | 27000 | 31000 | 35000 | 23000 |

We claim:

1. A separating agent for optical isomers comprising a polysaccharide derivative supported on a silica gel derivatized with a silylating agent of the formula (1):

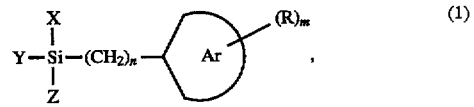

wherein at least one of X, Y and Z is Cl or an alkoxy group having 1 or 2 carbon atoms and the rest are methyl or ethyl group(s), n represents an integer of 1 to 8, R represents an alkyl or alkoxy group having 1 to 4 carbon atoms, m represents 0 or 1, and

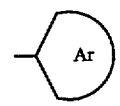

represents an aromatic group having 6 to 14 carbon atoms.

2. The separating agent according to claim 1, wherein the polysaccharide derivative is an ester or carbamate derivative of a polysaccharide selected from the group consisting of cellulose and amylose.

3. The separating agent according to claim 1, wherein the polysaccharide derivative is cellulose tris (4-methylbenzoate).

4. The separating agent of claim 1, wherein n in the general formula (1) is 2 to 4.

5. The separating agent of claim 1, wherein

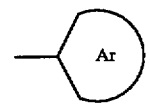

is a phenyl group.

6. The separating agent of claim 1, wherein the silica gel has a particle diameter of 1 μm to 10 mm and a pore diameter of 10 to 100 μm before the surface treatment.

7. The separating agent of claim 1, wherein the polysaccharide derivative is an ester or carbamate derivative of a polysaccharide.

8. A separating agent for optical isomers according to claim 1, which is used for reversed-phase liquid chromatography.

9. A process for separating an optical isomer from racemic compounds comprising the steps of contacting the racemic compounds with the separating agent for optical isomers as set forth in claim 1 and isolating the optical isomer from the racemic compounds.

10. The process of claim 9, which is conducted by reversed-phase liquid chromatography.

11. The separating agent according to claim 1, wherein the silylating agent is selected from the group consisting of 3-phenylpropyldimethylchlorosilane, methyl(2-phenethyl)dichlorosilane and 3-(4-methoxyphenyl)propylmethyldichlorosilane.

12. The separating agent according to claim 11, wherein said silica gel is further treated with a member selected from the group consisting of N,O-bis(trimethylsilyl)acetamide, trimethylchlorosilane and hexamethyldisilazane.

* * * * *